US011617840B2

(12) United States Patent
Miller et al.

(10) Patent No.: US 11,617,840 B2
(45) Date of Patent: Apr. 4, 2023

(54) SYSTEMS, DEVICES, AND METHODS INCLUDING VARYING VISCOSITY COSMETIC DISPENSER

(71) Applicant: L'OREAL, Paris (FR)

(72) Inventors: Zane Miller, Seattle, WA (US); Vincenzo Casasanta, Woodinville, WA (US); John Streeter, Redmond, WA (US)

(73) Assignee: L'OREAL, Paris (FR)

( * ) Notice: Subject to any disclaimer, the term of this patent is extended or adjusted under 35 U.S.C. 154(b) by 461 days.

(21) Appl. No.: 15/475,724

(22) Filed: Mar. 31, 2017

(65) Prior Publication Data

US 2018/0280633 A1 Oct. 4, 2018

(51) Int. Cl.
*A61M 11/00* (2006.01)
*A45D 34/04* (2006.01)
(Continued)

(52) U.S. Cl.
CPC ........... *A61M 11/005* (2013.01); *A45D 34/04* (2013.01); *A61M 11/003* (2014.02); *B05B 12/10* (2013.01);
(Continued)

(58) Field of Classification Search
CPC .............. A45D 2034/005; A45D 34/04; A45D 2200/057; A61M 11/003; A61M 2205/3317; A61M 2205/3561; A61M 2205/3584; A61M 2205/6027; A61M 2205/6054; A61M 2205/6072;
(Continued)

(56) References Cited

U.S. PATENT DOCUMENTS 7,841,335 B2 11/2010 Harrington et al.
2003/0196660 A1 10/2003 Haveri
(Continued)

FOREIGN PATENT DOCUMENTS

EP 2 197 313 B1 7/2011
EP 2 457 065 5/2012
(Continued)

OTHER PUBLICATIONS

International Search Report and Written Opinion of the International Searching Authority dated Jun. 26, 2018 in PCT/US2018/025367, citing documents AA-AD, AO and AP therein, 14 pages.
(Continued)

*Primary Examiner* — Rachel T Sippel
(74) *Attorney, Agent, or Firm* — Oblon, McClelland, Maier & Neustadt, L.L.P.

(57) ABSTRACT

An apparatus that includes at least one nebulizer that includes a mesh material having a plurality of pores, a vibrating actuator coupled to the nebulizer and configured to produce ultrasonic vibration when energized according to a set energy profile, and a reservoir receiver configured to receive a reservoir that holds a topical formulation, the reservoir being coupled to the nebulizer when received. When the nebulizer is placed in contact with the topical formulation, vibration of the mesh nebulizer by the vibrating actuator, according to the set energy profile, ejects droplets of the topical formulation from the plurality of pores, forming a spray.

21 Claims, 8 Drawing Sheets

(51) Int. Cl.
*H04L 9/40* (2022.01)
*B05B 17/00* (2006.01)
*B05B 12/10* (2006.01)
*H04B 5/00* (2006.01)
*A45D 34/00* (2006.01)

(52) U.S. Cl.
CPC ....... B05B 17/0646 (2013.01); H04B 5/0062 (2013.01); H04L 63/0428 (2013.01); *A45D 2034/005* (2013.01); *A61M 2205/3317* (2013.01); *A61M 2205/3561* (2013.01); *A61M 2205/3584* (2013.01); *A61M 2205/6027* (2013.01); *A61M 2205/6054* (2013.01); *A61M 2205/6072* (2013.01)

(58) Field of Classification Search
CPC ........ A61M 11/00–005; A61M 15/001; A61M 15/0085; A61M 37/0092; A61M 2205/3375; B05B 12/10; B05B 17/0646; B05B 17/06–0692; H04B 5/0062; H04L 63/0428
See application file for complete search history.

(56) References Cited

U.S. PATENT DOCUMENTS

| | | | | |
|---|---|---|---|---|
| 2005/0225201 | A1* | 10/2005 | Vogeley | F04B 43/046 310/317 |
| 2006/0198940 | A1* | 9/2006 | McMorrow | B05B 17/0646 427/2.1 |
| 2006/0198942 | A1* | 9/2006 | O'Connor | B05B 17/0646 427/2.1 |
| 2007/0054040 | A1* | 3/2007 | Drake | A61L 26/0023 427/180 |
| 2007/0163583 | A1* | 7/2007 | Brand | A61M 15/0065 128/203.23 |
| 2008/0011292 | A1* | 1/2008 | Sugita | A61M 5/16827 128/200.19 |
| 2009/0095821 | A1 | 4/2009 | Feriani et al. | |
| 2009/0264550 | A1* | 10/2009 | Rayner | B01D 67/0027 521/189 |
| 2009/0277971 | A1* | 11/2009 | Scott | B05B 17/0669 239/4 |
| 2011/0295215 | A1* | 12/2011 | Nielsen | G16H 20/17 604/257 |
| 2012/0266870 | A1 | 10/2012 | Denyer et al. | |
| 2014/0145000 | A1 | 5/2014 | Verschueren | |
| 2015/0069146 | A1* | 3/2015 | Lowy | B05B 15/58 239/102.2 |
| 2015/0079670 | A1 | 3/2015 | Domanski et al. | |
| 2015/0231340 | A1* | 8/2015 | Pumphrey | G01N 27/223 128/200.16 |
| 2016/0193345 | A1* | 7/2016 | Yum | A61K 9/4858 424/452 |
| 2016/0216712 | A1* | 7/2016 | Baumgartner | A61L 2/22 |
| 2018/0367905 | A1* | 12/2018 | Meng | H04R 7/04 |
| 2019/0134330 | A1* | 5/2019 | Germinario | A61M 16/107 |

FOREIGN PATENT DOCUMENTS

| | | |
|---|---|---|
| JP | 2013-510627 A | 3/2013 |
| JP | 2013-540555 A | 11/2013 |
| WO | WO 2011/058477 A1 | 5/2011 |
| WO | WO 2012/056398 A1 | 5/2012 |

OTHER PUBLICATIONS

Combined Chinese Office Action and Search Report dated Sep. 3, 2020 in Chinese Patent Application No. 201880022222.X, citing document AA therein, 10 pages.
Office Action dated Oct. 26, 2020 in Korean Application No. 10-2019-7028114 (w/English translation).
Japanese Office Action dated Oct. 13, 2020 in Japanese Patent Application No. 2019-548565 (with Engligh translation), citing documents AO and AP therein, 10 pages.
Office Action dated Apr. 10, 2021 in Korean Application No. 9-5-2021-031505564 (w/English translation).
European Office Action dated Dec. 22, 2021 in European Patent Application No. 18721531.4, 5 pages.

* cited by examiner

```
         Start
           ↓
  ┌─────────────────────────────────┐ ─ 502
  │ Control delivery of energy from │
  │   power source to mesh nebulizer│
  └─────────────────────────────────┘
           ↓
          End
```
500a

FIG. 5B

```
         Start
           ↓
  ┌─────────────────────────────────┐ ─ 510
  │ Detect impedance spectrum of    │
  │ combined topical and nebulizer  │
  │ system                          │
  └─────────────────────────────────┘
           ↓
  ┌─────────────────────────────────┐ ─ 512
  │ Determine an energy profile     │
  │ based on the detected impedance │
  │ spectrum of the system          │
  └─────────────────────────────────┘
           ↓
  ┌─────────────────────────────────┐ ─ 514
  │ Control delivery of energy from │
  │ power source to mesh nebulizer  │
  │ based on the determination      │
  └─────────────────────────────────┘
           ↓
          End
```
500b

SYSTEMS, DEVICES, AND METHODS INCLUDING VARYING VISCOSITY COSMETIC DISPENSER

BACKGROUND

The present disclosure describes a personal care appliance for use in skincare including an ultrasonic topical applicator.

SUMMARY

In an embodiment, an apparatus is provided comprising: at least one nebulizer that includes a mesh material having a plurality of pores; a vibrating actuator coupled to the nebulizer and configured to produce ultrasonic vibration when energized according to a set energy profile; a reservoir receiver configured to receive a reservoir that holds a topical formulation, the reservoir being coupled to the nebulizer when received, wherein when the nebulizer is placed in contact with the topical formulation, vibration of the mesh nebulizer by the vibrating actuator, according to the set energy profile, ejects droplets of the topical formulation from the plurality of pores, forming a spray.

In an embodiment, the apparatus further comprises circuitry configured to set the energy profile according to one or more inputs indicative of one or more rheological properties of the topical formulation.

In an embodiment, the apparatus further comprises circuitry configured to sense the impedance spectrum system with of a topical formulation contained in the reservoir, and the processing circuitry is configured to set the energy profile based on the sensed impedance spectrum.

In an embodiment, the energy profile is set based on predetermined power spectrum associated with the one or more rheological properties of the topical formulation.

In an embodiment, the apparatus further comprises a reader configured read information from the reservoir, and the processing circuitry is configured to set the energy profile based on the information obtained from the reader.

In an embodiment, the reader is a radio frequency identification (RFID) reader configured to obtain the information via near field communication (NFC) with a radio frequency identification (RFID) tag attached to the reservoir.

In an embodiment, the reader is a bar code reader configured to obtain the information via scanning a bar code attached to the reservoir.

In an embodiment, the reader is a contact reader configured to obtain the information via an integrated circuit attached to the reservoir.

In an embodiment, the at least one nebulizer includes at least two separate nebulizers coupled to at least two different vibrating actuators.

In an embodiment, the two separate nebulizers are coupled to two different reservoir receivers configured to receive a different respective reservoir that holds a different respective topical formulation.

In an embodiment, each of the different topical formulations has different rheological properties, and the vibrating actuator coupled to each of the nebulizers is configured to produce a different ultrasonic vibration when energized according to a different set energy profile based on the different rheological properties.

In an embodiment, the two separate nebulizers each have mesh material portions with different pore characteristics with respect to each other.

In an embodiment, the at least one nebulizer includes a plurality of different mesh material portions each having a plurality of pores with different characteristics.

In an embodiment, the apparatus further comprises circuitry configured to detect a topical formulation cartridge and to generate nebulizer control information responsive to one or more inputs indicative of a rheological property of a formulation within the topical formulation cartridge.

In an embodiment, the apparatus further comprises circuitry configured to exchange encrypted and anonymized information with a remote network.

In an embodiment, the apparatus further comprises circuitry configured to communicate with a client device to exchange encrypted and anonymized information with the client device.

In an embodiment, the apparatus further comprises circuitry configured to communicate with a client device to exchange encrypted and to exchange nebulizer control information with the client device.

In an embodiment, a method is provided, implemented by an apparatus having at least one nebulizer that includes a mesh material having a plurality of pores, a vibrating actuator coupled to the nebulizer and configured to produce ultrasonic vibration when energized according to a set energy profile, and a reservoir receiver configured to receive a reservoir that holds a topical formulation, the reservoir being coupled to the nebulizer when received, the method comprising: exposing the nebulizer to be in contact with the topical formulation, and controlling the vibration actuator, according to the set energy profile, to cause vibration of the mesh nebulizer to eject droplets of the topical formulation from the plurality of pores, forming a spray.

In an embodiment, the method further comprises setting set the energy profile according to one or more inputs indicative of one or more rheological properties of the topical formulation.

In an embodiment, the method further comprises sensing the impedance spectrum system with of a topical formulation contained in the reservoir, and setting the energy profile based on the sensed impedance spectrum.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein:

FIG. 1A is drawing of front view of an ultrasonic topical applicator including a housing having an aperture, a mesh nebulizer, and a user control interface according to an example;

FIG. 1B is drawing of side view of the ultrasonic topical applicator showing internal components including a cartridge having a reservoir for holding a topical, a controller, a power source, and circuitry according to an example;

FIG. 1C is drawing of front view of an ultrasonic topical applicator including a housing having an aperture, a first mesh nebulizer, a second mesh nebulizer, and a user control interface according to an example;

FIG. 1D shows a cross-section drawing of a cartridge having a reservoir including a predetermined topical and an identifier configured to encode or indicate the predetermined topical;

FIG. 2A is a drawing of a top view of a mesh nebulizer having a uniform mesh according to an example;

DETAILED DESCRIPTION

Ultrasonic mesh nebulizer technology is utilized in applicators, pulmonary inhalers, home misting and other devices intended to provide a fine spray for small particle size, greater distribution or surface coverage. An ultrasonic topical applicator device is provided for dispensing of a topical fluid/cosmetic based on a rheological property of the topical.

Many commonly-used materials and formulations of topicals can exhibit complex rheological properties, whose viscosity and viscoelasticity can vary depending upon the external conditions applied, such as stress, strain, timescale, and temperature. The rheological properties of topicals including fillers are determined not only by the type and amount of filler, but also by the shape, size and size distribution of its particles. Examples of topicals include fluids, cosmetics, sunscreen, perfumes, repellants, etc. In an example, the topical can have a known viscosity or topical viscosity. Examples of rheological properties include viscosity, density, surface tension, wetting angle, shear rate, hydrophobicity, and hydrophilicity.

In an example, the ultrasonic topical applicator device includes a mesh nebulizer having a thin metal mesh connected to a vibrating actuator configured to produce ultrasonic vibration when energized at an energy profile. When a surface of the mesh nebulizer is placed in contact with the topical, vibration of the mesh nebulizer is configured to eject droplets of the topical from the plurality of pores, forming a spray. The energy profile can be based on a rheological property of the topical.

Referring now to the drawings, wherein like reference numerals designate identical or corresponding parts throughout the several views.

Figure 1A:
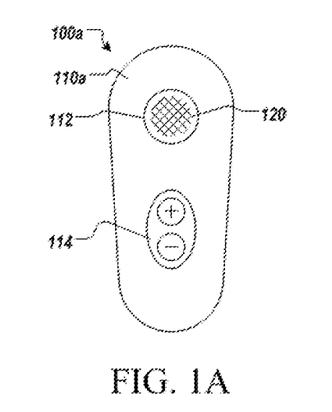
Figure 1B:
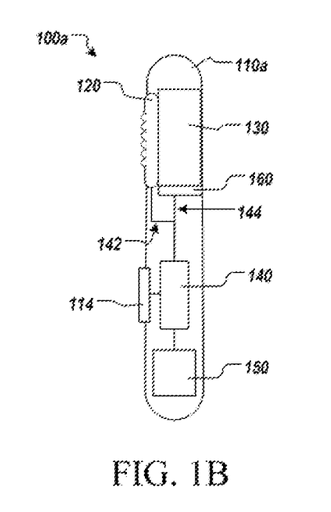
Figure 1C:
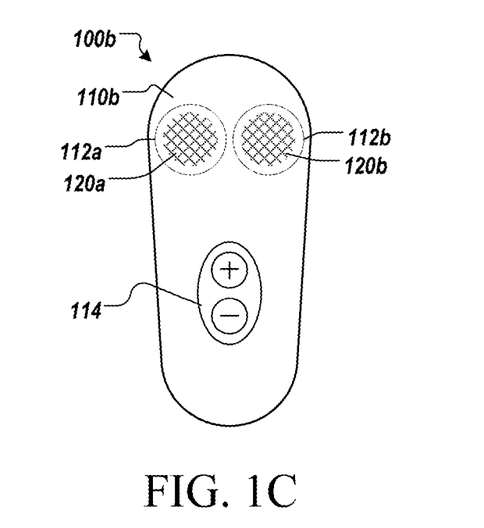
Figure 3A:
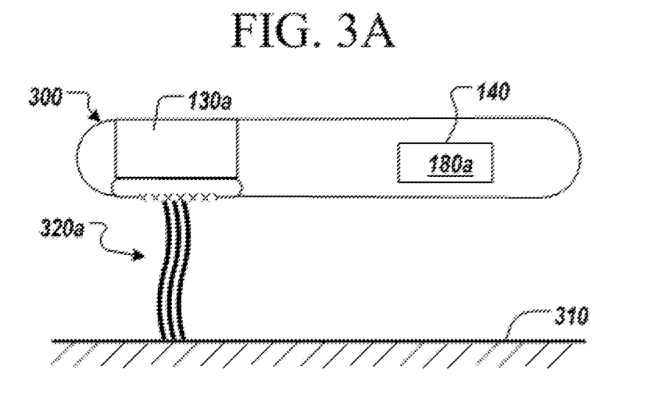
FIG. 3A shows a drawing of the ultrasonic topical applicator including a cartridge having a reservoir filled with a first topical configured to control energy delivered from the power source to the mesh nebulizer having the first mesh according to an example.
Figure 3B:
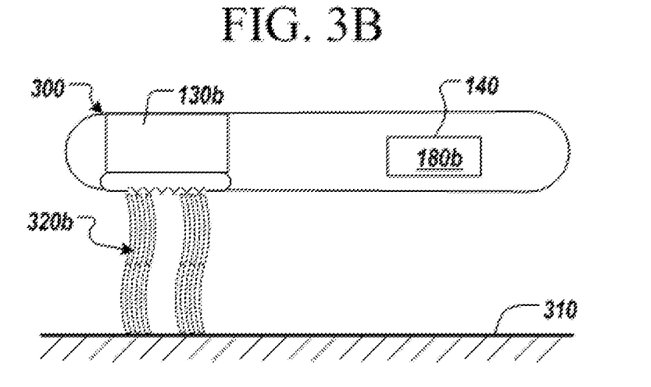
FIG. 3B shows a drawing of the ultrasonic topical applicator including a cartridge having a reservoir filled with a second topical configured to control energy delivered from the power source to the mesh nebulizer having the second mesh according to an example.

FIG. 1A is drawing of a front view of an ultrasonic topical applicator (UTA) device, shown as 100a and 100b in FIGS. 1A-1C, including a housing 110 having an aperture 112, a mesh nebulizer 120 having a plurality of pores, a cartridge 130 having a reservoir for holding a topical. In an example, the housing 110 can have a user control interface 114 configured to receive a user input, an indicator (not shown) configured to indicate a notice to the user. As shown in FIG. 1B, UTA device 100a further includes a controller 140 in communication with a power source 150, and circuitry 142, 144 configured to connect electrical components. In an example, the UTA device 100a is configured to eject a spray 320 (See FIGS. 3A-3B) using the controller 140 to control the energy profile 180 delivered from the power source 150 to the mesh nebulizer 120. The mesh nebulizer 120 is coupled to a cartridge 130 having a reservoir filled with a topical having a rheological property. The cartridge shown in FIG. 1B includes a tag (not shown) which can be used to identify the specific topical or the specific rheological property of the topical inside the cartridge. A reader 160 coupled to the controller 140 may be used to obtain the information to be conveyed by the tag. The tag may be an RFID tag from which the controller can obtain data, and the reader 160 may be an RFID reader coupled to the controller 140 which utilizes near field communication (NFC) technology, as is understood in the art. The tag may also include a bar code, and the reader 160 may be a bar code reader (not coupled to the controller 140, as is understood in the art. The reader 160 may be a contact reader configured to obtain the information via an integrated circuit attached to the reservoir, as is understood in the art.

FIG. 1C shows an alternative embodiment of a UTA device 100b which includes a housing 110b. The housing 110b accommodates two apertures 112a and 112b, and two mesh nebulizers 120a and 120b, respectively. With the two mesh nebulizers, two different cartridges 130 may be coupled thereto for providing two different topicals which are controlled to be sprayed by the controller 140 based on two different energy profiles based on their respective rheological properties. Two different tags may be affixed to each cartridge and reader with one or more readers 160 as described above for FIG. 1B.

Figure 1D:
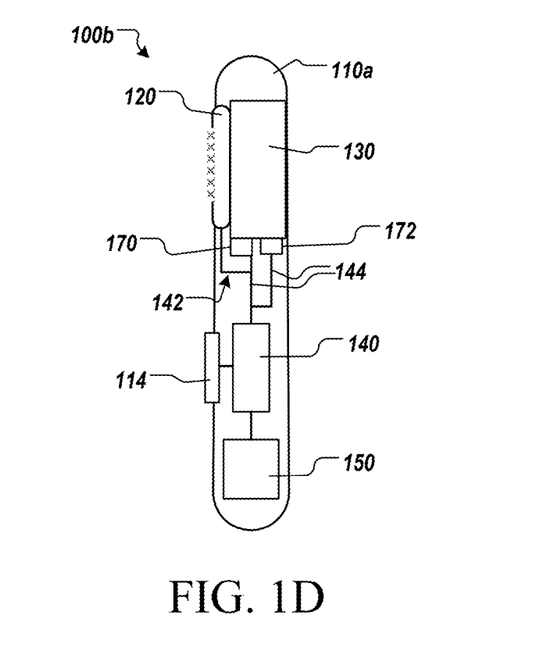

In an alternative embodiment shown in FIG. 1D, a sensing circuitry 170 may be disposed near the cartridges which is configured to determine a rheological property of the topical disposed in the cartridge. This type of sensor allows for the topical to be detected without the reliance of accurate or proprietary labeling or RFID coding of a tag associated with the cartridge.

Figure 4:
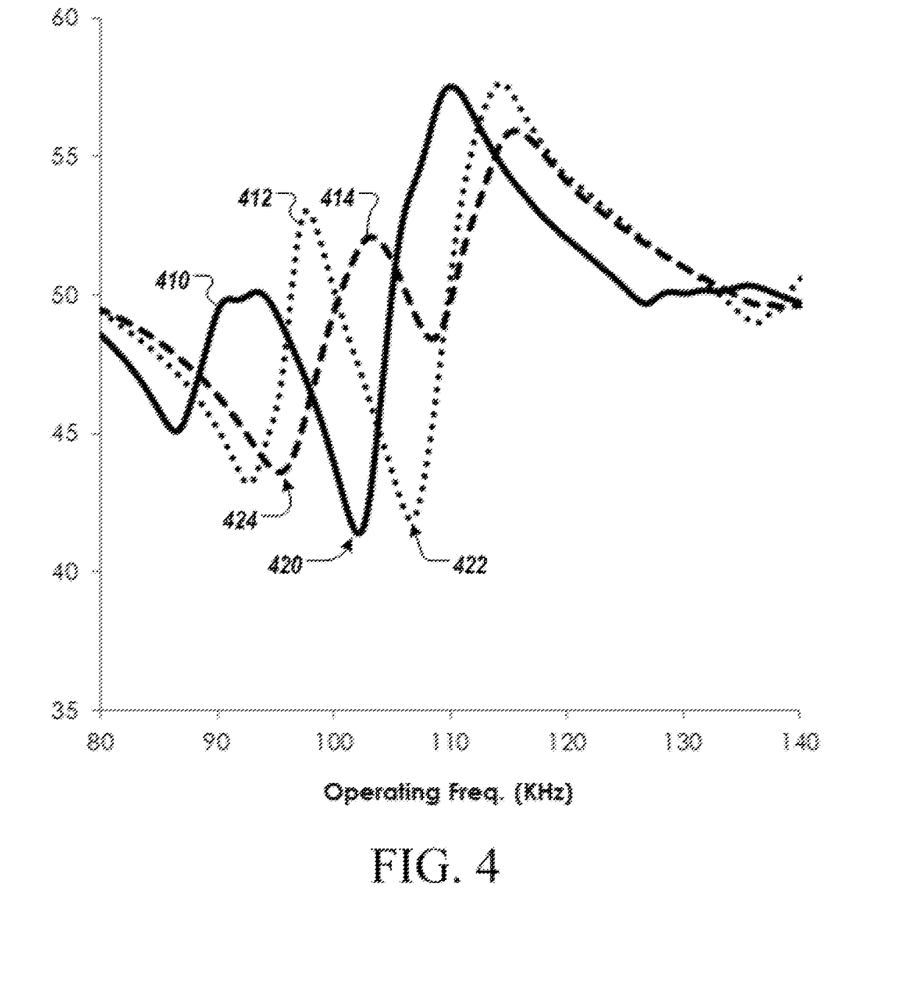
FIG. 4 shows a graph of a power spectrum for a set of topical having different rheological properties according to an example.

For example, sensing circuitry 170 is configured to detect the combined system impedance of the nebulizer in contact with the topical. This type of circuitry allows for the energy profile to be determined without the reliance of accurate or proprietary labeling or RFID coding of a tag associated with the cartridge. The energy profile may be correlated to a rheological property of the topical in the cartridge and can be used to determine the drive frequency of the vibrating actuator in the nebulizer, which is described below. A graph of a power spectrum for a set of topicals having different rheological properties is described below with respect to FIG. 4. The impedance detector circuitry sends an electrical signal through the system, sweeping through a frequency range within a defined band and measures the system impedance at each frequency. The frequency that corresponds to the lowest system impedance is the optimal drive frequency for the system. The energy profile to drive the device is then modified to operate at the frequency found by the impedance detection circuit.

In some implementations, the housing 110 can include one or more of an actuator, a valve, a controllable aperture, an electromechanical orifice, an aperture diaphragm, an electromechanical port, and the like. In an example, the housing 110 can include one or more electronic oscillators for controlling a nebulizer, an ultrasonic vibrating mesh, an electromechanical spray valve, and the like. In an example, the aperture 112 can act as a nozzle that can direct the spray in one direction or another (not shown).

Mesh Nebulizer

Figure 2A:
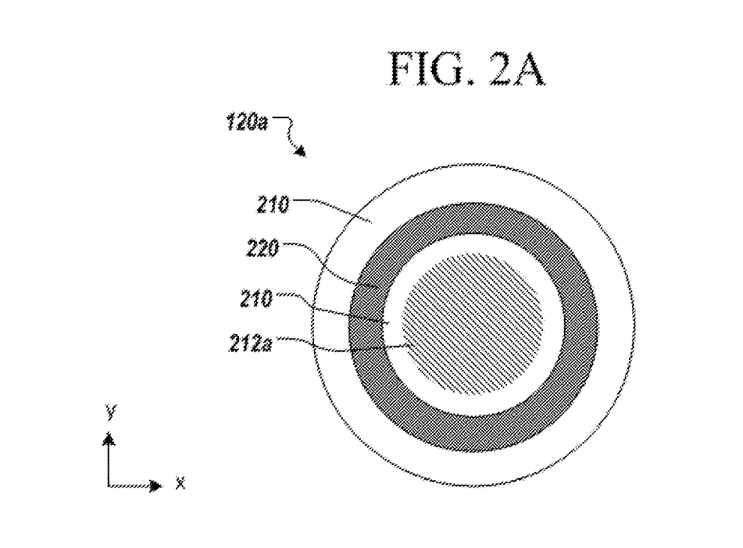
FIG. 2B is a drawing of a side view of the mesh nebulizer having a uniform mesh according to an example.
FIG. 2C is a drawing of a top view of a mesh nebulizer having a first mesh and a second mesh according to an example.
FIG. 2D is a drawing of a side view of a mesh nebulizer having the first mesh and the second mesh according to an example.
FIG. 2E is a drawing of a top view of a mesh nebulizer having a hybrid mesh according to another example.
FIG. 2F is a drawing of a side view of a mesh nebulizer having the hybrid mesh according to an example.
FIG. 2G is a drawing of a top view of a mesh nebulizer having a plurality of meshes according to another example.
Figure 2B:
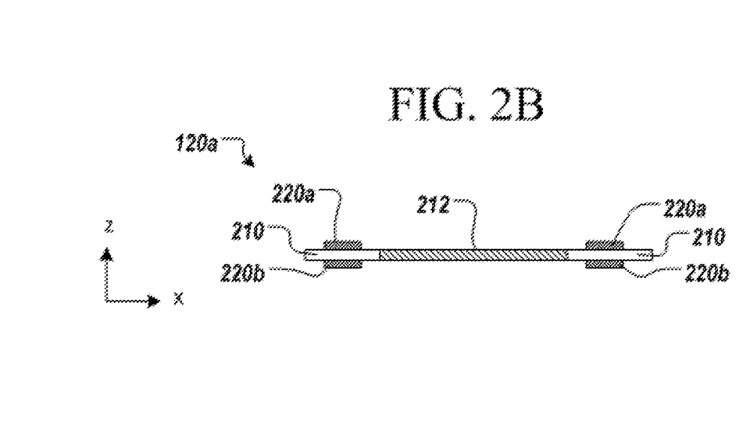
Figure 2C:
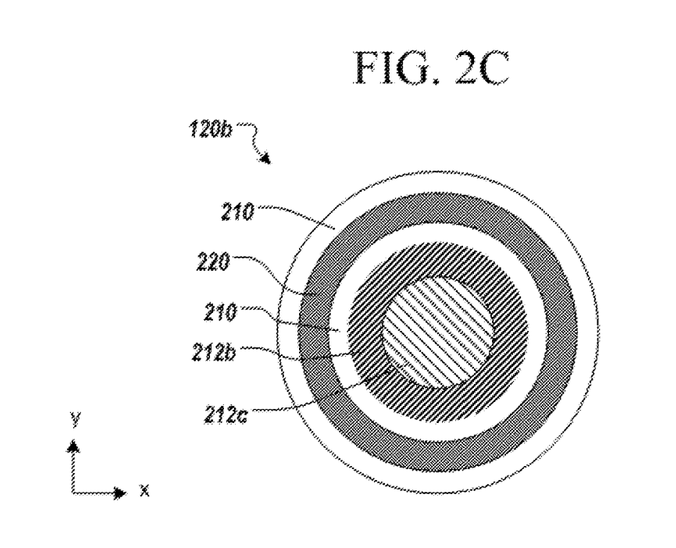
Figure 2D:
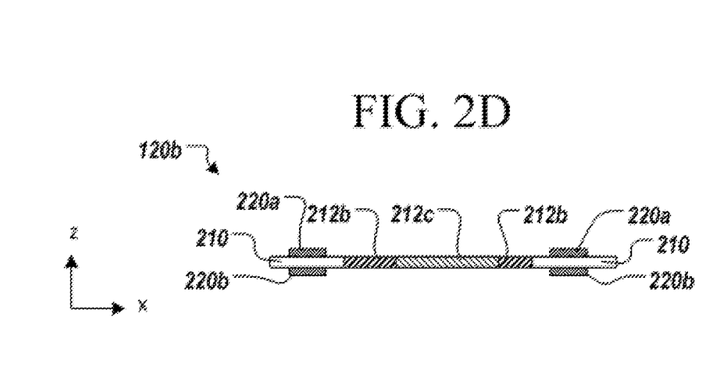
Figure 2E:
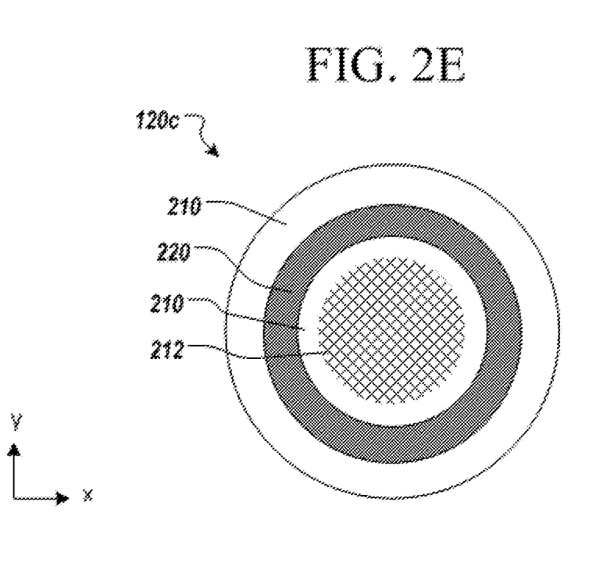
Figure 2F:
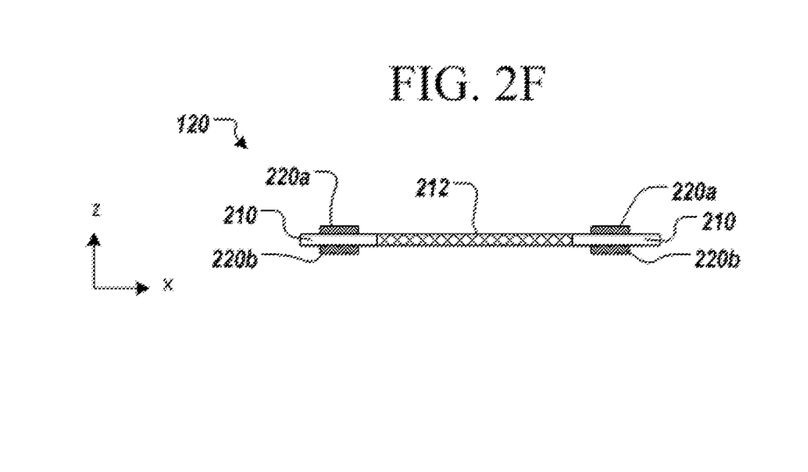
Figure 2G:
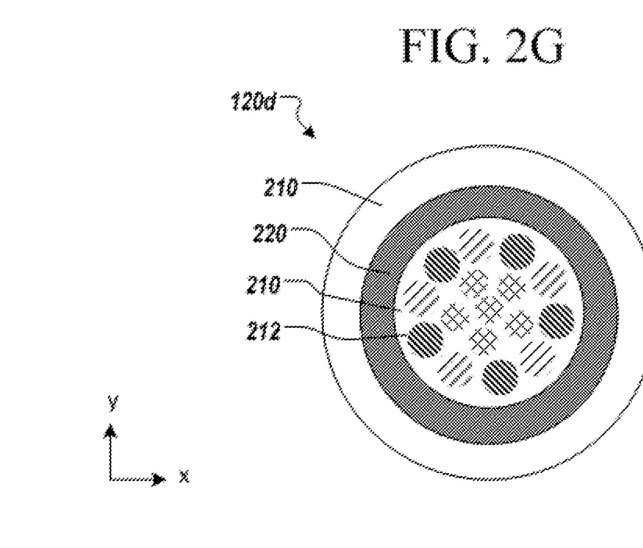

In some implementations, the mesh nebulizer 120 can be made from a perforated plate 210 having a mesh portion 212 and a vibrating actuator 220. In an example, the mesh 212 of the perforated plate 210 can be made from a plurality of pores through the perforated plate 210. In an example, the perforated plate 210 can be made from a thin metal, a polymer or a ceramic configured to vibrate at ultrasonic frequencies. In an example, the mesh nebulizer 120 can be a microporous atomizer high output mesh from Steiner & Martins, INC. (Doral, Fla.). In another example, the mesh nebulizer 120 can be an ultrasonic atomizer from Shenzhen Hurricane (China). In another example, the mesh nebulizer 120 can be an ultrasonic atomizer from MicroBase Technology Corp. (Taiwan).

In an aspect, each pore can be configured to prevent leaking of the topical. In an example, each pore can be configured to eject the topical based on the topical rheology. In an example, each pore can have a circular shape with a diameter of 5μ to 20μ. In an example, the plurality of pores can be laser drilled through the perforated plate 210. In another example, the perforated plate 210 can be manufactured with the plurality of pores using Microelectromechanical systems (MEMS) processing technology.

FIGS. 2A-2B each show a drawing of a top and side view respectively of a mesh nebulizer 120*a* having a disk shape according to an example. In an example, the vibrating actuator 220 is made of a piezoelectric material bonded to at least one side of the perforated plate 210. As best shown is FIG. 2B, the vibrating actuator 220 can be made from a top piezoelectric material 220*a* and a bottom piezoelectric material 220*b* that sandwich the perforated plate 210.

FIGS. 2C-2D show an alternative embodiment in which mesh portion 212 comprises two different mesh regions 212*b* and 212*c*. The different mesh regions may have different properties, such as a different pore shape, pore diameter, pore spacing, or different thickness of material. While FIG. 2C shows that there are two different mesh regions concentrically disposed with respect to one another, there may be additional mesh regions and they may be disposed in any number of patterns.

FIGS. 2E-2F show an alternative embodiment in which the mesh portion 212 includes a larger pore size than that of FIG. 2A. Such a different pore size may be used in a second mesh nebulizer in the UTA device of FIG. 1C, or as the standalone mesh nubulizer in FIG. 1A. The pores may also be adjustable in size. For instance, there may be two superimposed meshes in the aperture, where an orifice size of each pore is changed by sliding one over the other to change the exposed hole shape. Alternatively, the mesh could be configured to be stretched to change the hole diameter. Further, the mesh could have addressable MEMS structures for exposing/occluding holes, changing hole shape, or the like.

FIG. 2G shows an alternative embodiment, in which the mesh portion includes different mesh regions 212 that are scattered in a predetermined pattern. The mesh regions 212 may be scattered within the perforated plate material 210 to target the spray specified manner. While FIG. 2G shows five mesh regions in a circular pattern, any number of patterns may be used based on a specified application or desired treatment.

Controller

In an example, the UTA device 100*a* is configured to dispense or eject a topical spray 320 by using the controller 140 to control the energy delivered from the power source 150 to the mesh nebulizer 120.

FIG. 3A shows a drawing of an ultrasonic topical applicator 300 having the mesh nebulizer 120*b*, a cartridge 130*a* having a reservoir filled with a first topical having a first rheological property and a controller 140 configured to control energy delivered from the power source to the mesh nebulizer in order to create spray 320*a* towards a skin 310 of a user using an energy profile 180*a*, where the energy profile 180*a* is based on the first rheological property.

FIG. 3B shows a drawing of the ultrasonic topical applicator 300 having the mesh nebulizer 120*b*, a cartridge 130*b* having a reservoir filled with a second topical having a second rheological property and a controller 140 configured to control energy delivered from the power source to the mesh nebulizer in order to create spray 320*b* using an energy profile 180*b*, where the energy profile 180*b* is based on the second rheological property.

In some implementations, the controller 140 is configured to control the energy profile 180 for delivering energy from the power source 150 to the mesh nebulizer 120 based on at least one of a impedance detector (described above) and a cartridge sensor. The cartridge sensor may include sensor circuitry to detect one or more of the following: (i) the presence of a cartridge, which could be based on a contact sensor for example; and (ii) the amount of fluid in the cartridge, which could be based on a load sensor 172 (see FIG. 1D). In some embodiments, the controller 140 incudes a programmable microcontroller or processor (not shown), which is configured to control the energy delivered from the power source 150 to the mesh nebulizer 120.

In an example, the energy profile 180 is configured to cause the vibrating actuator 220 to produce ultrasonic vibration based on a frequency and power. A representative energy profile 180 can include a frequency of about 120 KHz and power of about 5 W.

In an example, the energy profile 180 can vary an intensity of the spray 320. In an example, the energy profile 180 can be based on a type of topical or the topical viscosity. In an example, the energy profile 180 can be determined by sensing an identifier or a cartridge sensor as described below. In an example, the energy profile 180 can be determined by receiving an input from the user control interface 114.

FIG. 4 shows a graph of a power spectrum for a set of topicals having different rheological properties according to an example. Line 410 shows the impedance curve for a given transducer with a nanoemulsion sunscreen formula in the reservoir. Line 412 shows the impedance curve for a given transducer with DI H2O in the reservoir. Line 414 shows the impedance curve for a given transducer with an alcohol and oil based sunscreen formula in the reservoir. Points 420, 422 and 424 show local minima impedance, indicating the resonant frequency of the system for each formula, which in turn is the optimal drive frequency for each formula.

Method for Dispensing a Topical

Figure 5A:
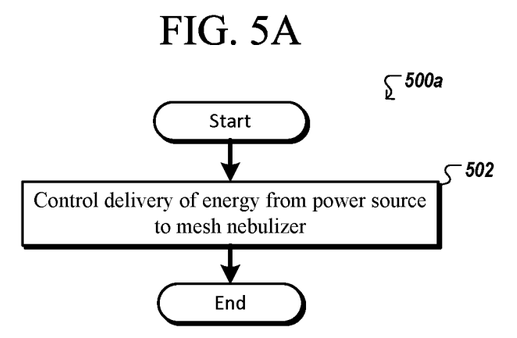
FIG. 5A is a flow diagram describing a method for dispensing a topical according to an example.
Figure 5B:
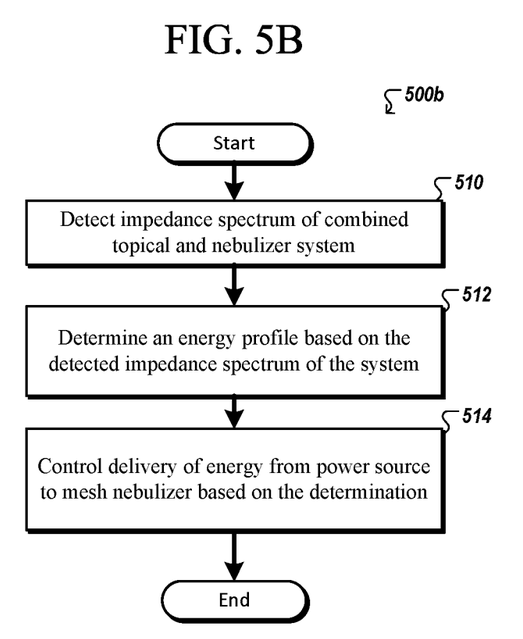
FIG. 5B is a flow diagram describing a method for dispensing a topical based on detecting an impedance spectrum of the combined topical and nebulizeraccording to an example.
Figure 5C:
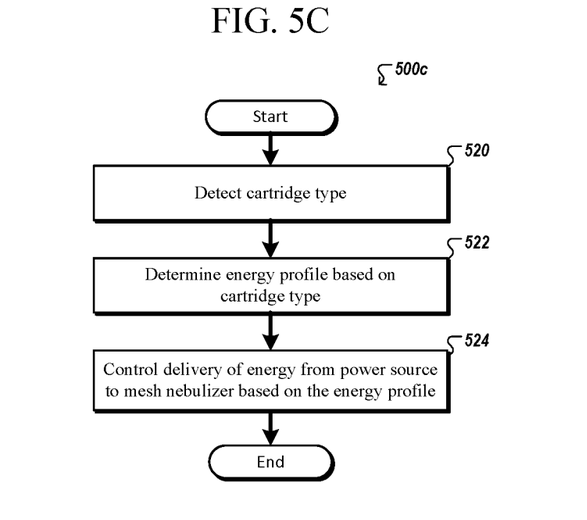
FIG. 5C is a flow diagram describing a method for dispensing a topical based on a cartridge type according to an example.
Figure 5D:
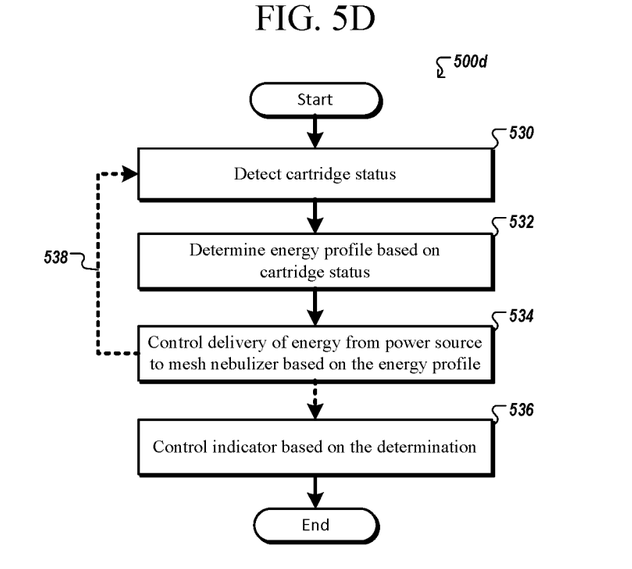
FIG. 5D is a flow diagram describing a method for dispensing a topical based on a cartridge status according to an example.

FIG. 5A is a flow diagram describing a method 500a for dispensing a topical according to an example. The method 500a includes a step of controlling delivery of energy from a power source 150 to a mesh nebulizer 120 (502). An example of step 502, controlling delivery of energy from the power source 150 to the mesh nebulizer 120, can be configured to use a predetermined energy profile 180. An example of step 502, can be controlling, using a controller 140, delivery of energy based on an energy profile 180 from a power source 150 to a mesh nebulizer 120 having a perforated plate with a plurality of pores and a vibrating actuator. The vibrating actuator is configured to produce an ultrasonic vibration based on the energy profile 180, where the topical is nebulized when in contact with the perforated plate vibrating with the ultrasonic vibration, and where the nebulized topical forms a spray dispensing the topical.

In an example, the predetermined energy profile 180 can be set using the user control interface 114. In another example, the predetermined energy profile 180 can be encoded on the cartridge and read using the sensor.

Dispensing a Topical Based on a Impedance Spectrum of the Topical Combined with Nebulizer FIG. 5B is a flow diagram describing a method 500*b* for dispensing a topical based on an impedance spectrum of the system including a topical in contact with a nebulizer according to an example. The method 500*b* includes steps reading impedance spectrum of combined topical and nebulizer system (510), determining an energy profile 180 based on the impedance spectrum of the system (512), and controlling delivery of energy from the power source 150 to the mesh nebulizer 120 based on the determination of the energy profile (514). As an example of step 512, determining an energy profile 180 based on the detected impedence may include determining a frequency value and/or power level of an energy profile 180.

Dispensing a Topical Based on a Cartridge Type

FIG. 5C is a flow diagram describing a method 500*c* for dispensing a topical based on a cartridge type according to an example. The method 500*c* includes steps of detecting a cartridge type (520), determining an energy profile 180 based on the cartridge type (522), and controlling delivery of energy from the power source 150 to the mesh nebulizer 120 based on the energy profile 180 (524).

An example of step 522, determining an energy profile 180 based on the cartridge type, can be modifying a frequency and/or power of the energy profile 180 based on the topical type identified by the identifier.

Dispensing a Topical Based on a Cartridge Status

FIG. 5D is a flow diagram describing a method 500*d* for dispensing a topical based on a cartridge status according to an example. The method 500*d* includes steps of detecting a cartridge status (530), determining an energy profile 180 based on the cartridge status (532), and controlling delivery of energy from the power source 150 to the mesh nebulizer 120 based on the determination 532 or the energy profile 180 (534). Optionally, the method 500*d* can further include a step of controlling an indicator 116 based on the determination 532 (536). Optionally, the method 500*d* can further include a step of returning to step 530 (538).

An example of step 532, determining an energy profile 180 based on the cartridge status, can be modifying a frequency and/or power of the energy profile 180 based on the amount of topical in the reservoir 130 sensed by the cartridge sensor.

Additional Features

In an example, the cartridge sensor described above may provide an alert via indicator 116 based on determining that a cartridge is not inserted or is not inserted correctly. An alert may also be provided when the cartridge sensor detects that the amount of topical in the reservoir 130 sensed by the cartridge sensor is below a particular amount.

Furthermore, the circuitry of the main unit or the detachable unit of the personal cosmetic appliance 100*a* may be configured to actuate a discovery protocol that allows the main unit or the detachable unit and a remote enterprise to identify each other and to negotiate one or more pre-shared keys, which further allows the main unit or the detachable unit and a remote network to exchanged encrypted and anonymized information. The discovery protocol may further allow the main unit or the detachable unit and a remote network to exchange treatment regimen information depending on the type of applicator included in the detachable unit.

Furthermore, the circuitry of the UTA device may be configured to exchange control commands with a remote network via a communication interface, such that a remote client device may externally control the UTA device. For instance, the circuitry of the UTA device may be configured to exchange encrypted and anonymized information with a remote network. The circuitry of the UTA device may be configured to communicate with a client device to exchange encrypted and anonymized information with the client device. The circuitry of the UTA device may be configured to communicate with a client device to exchange encrypted and to exchange nebulizer control information with the client device. The circuitry of the UTA device may also be configured to detect the presence of the client device when the client device is active and within a certain range of the UTA device.

In an aspect, the client device described above can be in communication with a network and enable the user interface access to the Internet as well as Internet of Things (IOT). As can be appreciated, the network can be a public network, such as the Internet, or a private network such as an LAN or WAN network, or any combination thereof and can also include PSTN or ISDN sub-networks. The network can also be wired, such as an Ethernet network, or can be wireless such as a cellular network including EDGE, 3G and 4G wireless cellular systems. The wireless network can also be WiFi, Bluetooth, or any other wireless form of communication that is known. In an example, the network can access a server hosting media, protocols, products, personal accounts, stored usage data, and other data related to the UTA device.

To accomplish the above-described connectivity, the UTA device may include an external communication interface (not shown) for communicating with devices or networks external to the UTA device. In an example, the communication interface (I/F) can include circuitry and hardware for communication with a client device. The communication interface may include a network controller such as BCM43342 Wi-Fi, Frequency Modulation, and Bluetooth combo chip from Broadcom, for interfacing with a network.

The hardware for the controller 140 can be circuitry designed for reduced size. For example, the controller 140 may be a CPU as understood in the art. For example, the processor may be an APL0778 from Apple Inc., or may be other processor types that would be recognized by one of ordinary skill in the art. Alternatively, the CPU may be implemented as an FPGA, ASIC, PLD, embedded processor or using discrete logic circuits, as one of ordinary skill in the art would recognize. Further, the CPU may be implemented as multiple processors cooperatively working in parallel to perform the instructions of the inventive processes described above. The client device described above may also have similar circuitry and hardware as described above.

Obviously, numerous modifications and variations of the present disclosure are possible in light of the above teachings. It is therefore to be understood that within the scope of the appended claims, the invention may be practiced otherwise than as specifically described herein.

What is claimed is:

1. An apparatus comprising:
   at least one nebulizer that includes at least one mesh material having a plurality of pores;
   at least one vibrating actuator coupled to the at least one nebulizer and configured to produce ultrasonic vibration when energized according to a set energy profile;
   at least one reservoir receiver configured to receive at least one reservoir that holds a topical formulation, the at least one reservoir being coupled to the at least one nebulizer when received, wherein when the at least one nebulizer is placed in contact with the topical formulation, vibration of the mesh of the at least one nebulizer by the at least one vibrating actuator, according to the set energy profile, ejects droplets of the topical formulation from the plurality of pores, forming a spray; and
   at least one contact sensor configured to detect a presence of the at least one reservoir,
   wherein the energy profile determines a drive frequency of the at least one vibrating actuator that is correlated to one or more rheological properties of the topical formulation,
   wherein a single nebulizer of the at least one nebulizer includes a plurality of different mesh material portions, from the at least one mesh material, each having a plurality of pores with different characteristics, the different mesh material portions being scattered over the at least one mesh material in a predetermined pattern, and
   the apparatus further comprising:
   circuitry configured to transmit an electrical signal through the apparatus, sweeping through a frequency range within a defined band and measure the impedance at each frequency, detect a frequency that corresponds to the lowest measured impedance as an optimal drive frequency, and set the energy profile to include the optimal drive frequency as the drive frequency corresponding to the topical formulation in the detected reservoir;
   a reader configured to read information from the at least one reservoir, the circuitry configured to set the energy profile based on the information obtained from the reader; and
   at least one load sensor configured to detect an amount of topical formulation in the at least one reservoir, wherein the circuitry is configured to modify the drive frequency included in the energy profile based on the amount of topical in the reservoir sensed by the at least one load sensor.

2. The apparatus according to claim 1, wherein the energy profile is set based on a predetermined power spectrum associated with the one or more rheological properties of the topical formulation.

3. The apparatus according to claim 1, wherein the reader is a radio frequency identification (RFID) reader configured to obtain the information via near field communication (NFC) with a radio frequency identification (RFID) tag attached to the at least one reservoir.

4. The apparatus according to claim 1, wherein the reader is a bar code reader configured to obtain the information via scanning a bar code attached to the at least one reservoir.

5. The apparatus according to claim 1, wherein the reader is a contact reader configured to obtain the information via an integrated circuit attached to the at least one reservoir.

6. The apparatus according to claim 1, wherein the at least one nebulizer includes at least two separate nebulizers and the at least one vibrating actuator includes at least two different vibrating actuators respectively coupled to the at least two separate nebulizers.

7. The apparatus according to claim 6, wherein the at least one reservoir includes two different reservoirs that are coupled respectively to the two separate nebulizers and that each hold a different respective topical formulation.

8. The apparatus according to claim 7, wherein each of the different topical formulations has different rheological properties, and the vibrating actuator coupled to each of the nebulizers of the two separate nebulizers is configured to produce a different ultrasonic vibration when energized according to a different set energy profile based on the different rheological properties.

9. The apparatus according to claim 6, wherein the two separate nebulizers each have mesh material portions with different pore characteristics with respect to each other.

10. The apparatus according to claim 1, further comprising:
    the circuitry configured to detect a topical formulation cartridge and to generate nebulizer control information responsive to one or more inputs indicative of a rheological property of a formulation within the topical formulation cartridge.

11. The apparatus according to claim 1, further comprising:
    the circuitry configured to exchange encrypted and anonymized information with a remote network.

12. The apparatus according to claim 1, further comprising:
    the circuitry configured to communicate with a client device to exchange encrypted and anonymized information with the client device.

13. The apparatus according to claim 1, further comprising:
    the circuitry configured to communicate with a client device to exchange encrypted and to exchange nebulizer control information with the client device.

14. The apparatus according to claim 1, wherein the plurality of pores are adjustable in size.

15. The apparatus according to claim 14, wherein the plurality of pores are adjustable based on the at least one mesh material including two superimposed meshes being configured to slide over one another to change an exposed hole shape.

16. The apparatus according to claim 14, wherein the plurality of pores are adjustable based on the at least one mesh material being configured to be stretched to change a hole diameter.

17. A method, implemented by an apparatus having at least one nebulizer that includes a mesh material having a plurality of pores, a vibrating actuator coupled to the at least one nebulizer and configured to produce ultrasonic vibration when energized according to a set energy profile, and a reservoir receiver configured to receive a reservoir that holds a topical formulation, the reservoir being coupled to the at least one nebulizer when received, the method comprising:

detecting, with at least one contact sensor, a presence of the reservoir,     exposing the at least one nebulizer to be in contact with the topical formulation, and controlling the vibration actuator, according to the set energy profile, to cause vibration of the mesh of the at least one nebulizer to eject droplets of the topical formulation from the plurality of pores, forming a spray,     wherein the energy profile determines a drive frequency of the vibrating actuator that is correlated to one or more rheological properties of the topical formulation,     wherein a single nebulizer of the at least one nebulizer includes a plurality of different mesh material portions, with flat top and bottom surfaces, which have a different thickness of mesh material, from the at least one mesh material, each having a plurality of pores with different characteristics, the different mesh material portions being scattered over the at least one mesh material in a predetermined pattern, and     wherein the method includes     transmitting, by circuitry, an electrical signal through the apparatus, sweeping through a frequency range within a defined band and measure the impedance at each frequency, detecting a frequency that corresponds to the lowest measured impedance as an optimal drive frequency, and setting the energy profile to include the optimal drive frequency as the drive frequency corresponding to the topical formulation in the detected reservoir,     reading, with a reader, information from the at least one reservoir, the circuitry setting the energy profile based on the information obtained from the reader; and     detecting, by at least one load sensor, an amount of topical formulation in the at least one reservoir, wherein the circuitry modifies the drive frequency included in the energy profile based on the amount of topical in the reservoir sensed by the at least one load sensor.

18. The method according to claim 17, wherein the energy profile is set based on a predetermined power spectrum associated with the one or more rheological properties of the topical formulation.

19. The method according to claim 17, wherein the reader is a radio frequency identification (RFID) reader configured to obtain the information via near field communication (NFC) with a radio frequency identification (RFID) tag attached to the reservoir.

20. The method according to claim 17, wherein the reader is a bar code reader configured to obtain the information via scanning a bar code attached to the reservoir.

21. The method according to claim 17, wherein the reader is a contact reader configured to obtain the information via an integrated circuit attached to the reservoir.

\* \* \* \* \*